(12) United States Patent
Kawada et al.

(10) Patent No.: US 6,586,022 B2
(45) Date of Patent: Jul. 1, 2003

(54) THERAPEUTIC AGENT FOR TREATING ULCERATIVE COLITIS

(75) Inventors: Mitsuhiro Kawada, Kagawa (JP); Ken-ichi Hattori, Kagawa (JP); Shunji Aono, Toyonaka (JP)

(73) Assignee: Teikoku Seiyaku Co., Ltd., Kagawa (JP)

( * ) Notice: Subject to any disclaimer, the term of this patent is extended or adjusted under 35 U.S.C. 154(b) by 0 days.

(21) Appl. No.: 09/924,539

(22) Filed: Aug. 9, 2001

(65) Prior Publication Data

US 2002/0025351 A1 Feb. 28, 2002

Related U.S. Application Data

(62) Division of application No. 09/341,185, filed on Aug. 10, 1999.

(30) Foreign Application Priority Data

Nov. 4, 1997 (JP) .............................................. 9-316629
Nov. 2, 1998 (WO) ................................ PCT/JP98/04950

(51) Int. Cl.[7] .............................................. A61K 35/78
(52) U.S. Cl. ........................ 424/773; 424/725; 424/747; 424/756; 424/757
(58) Field of Search ................................ 424/773, 725, 424/747, 756, 757

(56) References Cited

FOREIGN PATENT DOCUMENTS

| JP | 62-26229 | 2/1987 |
|----|----------|--------|
| JP | 02-152926 | 6/1990 |
| JP | 06-40931 | 2/1994 |

OTHER PUBLICATIONS

Derwent English abstract of Chinese Pat. Appl. No. 1121422 A (May 1996).*

Michiaki Yakazu, "Applied Clinical Medicine: Guide for Chinese Medicine Formulation (in Japanese)", Sogen–sha, issued Jul. 20, 1977, 1st edition, 9th print, p. 78–82, 421–426, 234–240, 132–138.

* cited by examiner

Primary Examiner—Francisco Prats
Assistant Examiner—Susan D Coe
(74) Attorney, Agent, or Firm—Crowell & Moring LLP

(57) ABSTRACT

An ulcerative colitis treating therapeutic agent which is very effective in repairing damaged tissues of ulcerative colitis and yet has no need of fear of side effects as those of steroids is provided. It is an therapeutic agent for treating ulcerative colitis which has peony root, especially, dry powders of peony root, or a Chinese medicine formulation containing peony root as an active ingredient. It is also an therapeutic agent for treating ulcerative colitis which has, as an active ingredient, an infused dry extract of peony root, an infused dry extract of a Chinese medicine formulation containing peony root, or especially an infused dry extract of Jia-Wei-Xiao-Yao-San, Dang-Gui-Shao-Yao-San, Shao-Yao-Gan-Cao-Tang, or Gui-Zhi-Fu-Ling-Wan.

10 Claims, No Drawings

THERAPEUTIC AGENT FOR TREATING ULCERATIVE COLITIS

This application is a division of application Ser. No. 09/341,185, filed Aug. 10, 1999.

TECHNICAL FIELD

The present invention relates to a therapeutic agent for treating ulcerative colitis, which contains peony root. More particularly, the invention relates to a therapeutic agent for treating ulcerative colitis, having peony root or a Chinese medicine formulation containing peony root, which is very effective in repairing damaged tissues of ulcerative colitis and yet has no fear of side effects as those of steroids.

BACKGROUND ART

Ulcerative colitis is a diffuse nonspecific inflammatory disease that only causes inflammation mainly in large intestines, that is, the regions from the rectum to the intestinum cecum and is characterized by continuous lesion. The disease is characterized in that the region of inflammation is localized in mucosa and submucosa, remission and exacerbation are repeated, and it cannot be completely cured. From the characteristics, it is said that patients can be relatively easily diagnosed as ulcerative colitis.

With respect to the cause of ulcerative colitis, although there are various theories such as a theory that it is caused by food and life style and a theory that the cause is autoimmunity, the cause has not been convinced yet and the true cause is still unknown. Meanwhile, the enlargement process of inflammation of ulcerative colitis has been uncovered to a considerable extent and its knowledge has been disclosed in literatures, academic meetings, and the like. Ulcerative colitis cannot be treated by etiotropic therapy as a matter of fact and is treated by conservative therapy under the present conditions.

At present, drugs based on the knowledge of the uncovered enlargement process of the inflammation of ulcerative colitis are being actively developed. For example, clinical development tests of leukocyte removing therapy, lymphocyte removing therapy, anti-CD4 antibody, anti-TNF-α antibody and the like are being progressed.

In treatment of ulcerative colitis in actual clinical places, however, sulufasalazine (trade name: Salazopyrin) as a Sulfa drug or steroids which have been used for a long time is mainly administered. Treatment is given in which administration of the drugs, nutrition control, mental control, and the like are combined, and when it is still ineffective, surgical treatment is added. Such treatment is mainly given.

As for sulufasalazine and steroids used for drug therapy, sulufasalazine is relatively effective to patients with mild colitis and is used as a drug which is chosen first for the treatment of ulcerative colitis. The effect is, however, relatively weak on patients with severe colitis. Patients with mild colitis are often treated with both of sulufasalazine and steroids. In treatment in a remission phase of inflammation, in most cases, the combination of the drugs is switched to medication of only sulufasalazine. At an acute phase of inflammation, the medication of only sulufasalazine is often insufficient to produce an effect.

On the other hand, steroids often produce an excellent effect and are drugs mainly used in internal treatment. As its side effects have been known conventionally, it is necessary to be careful at the time of administration of steroids. It is also necessary to be very careful at the time of stopping the administration, what is called a withdrawal.

Although 5-ASA (5-aminosalicylate) which is considered to be an effective active part of sulufasalazine is clinically used, problems similar to those of sulufasalazine are also pointed out.

In view of the present conditions of treatment of ulcerative colitis, it is therefore an object of the invention to provide a therapeutic agent for treating ulcerative colitis, which is very effective in repairing tissues in an inflammatory region and yet exerts no side effects as those of steroids as a treatment agent based on the knowledge of the uncovered enlargement process of inflammation of ulcerative colitis.

Recently, a number of attempts to use Chinese herbal medicine to treat patients with ulcerative colitis are being made and a number of the following results have been published such as a case of enhancing anti-inflammatory power of, for example, steroids together with the medicine treatment ("Journal of society of Japanese and Chinese medical treatment" Vol. 8, p516, 1991; and Japanese Unexamined Patent Application No. 6-40931), a case of obtaining mental stability ("Gendai Toyo Igaku (Modern oriental medicine)", Vol. 13, No. 1, p125, 1992), a case of improving constipation, diarrhea, and the like ("Gendai Toyo Igaku (Modern oriental medicine)", Vol. 12, No. 1, p115, 1991), and description of the direct effect of inflammation remission by administration of Ren-Shen-Tang (Ninjin-to) ("Nihon Toyo Igaku Zasshi (Magazine of Japan Oriental Medicine)", Vol. 42, No. 3, p337, 1992).

The inventors have paid attention to effects of treatment of ulcerative colitis by Chinese herbal medicine and have wholeheartedly studied. As a result, they have newly found that, among Chinese herbal medicine, peony root and Chinese medicine formulations containing peony root such as Jia-Wei-Xiao-Yao-San (Kami-shoyo-san), Dang-Gui-Shao-Yao-San (Toki-shakuyaku-san), Shao-Yao-Gan-Cao-Tang (Shakuyaku-kanzo-to), and Gui-Zhi-Fu-Ling-Wan (Keishibukuryo-gan) act on promotion of repairing tissues in an inflammatory region of ulcerative colitis and come to achieve the prevent invention.

DISCLOSURE OF INVENTION

In order to solve the problems, therefore, the invention provides a therapeutic agent for treating ulcerative colitis containing peony root as an active ingredient. As a specific embodiment, a therapeutic agent for treating ulcerative colitis containing dry powders of peony root as an active ingredient is provided.

As another embodiment of the present invention, it is provided a therapeutic agent for treating ulcerative colitis having a Chinese medicine formulation containing peony root as an active ingredient wherein, more particularly, the Chinese medicine formulation containing peony root is Jia-Wei-Xiao-Yao-San, Dang-Gui-Shao-Yao-San, Shao-Yao-Gan-Cao-Tan, or Gui-Zhi-Fu-Ling-Wan.

Peony root as an active ingredient of an ulcerative colitis treatment agent provided by the present invention may take forms of not only the peony root dry powders and the Chinese medicine formulation containing peony root as described above but also an infused dry extract of peony root or Chinese medicine formulation containing peony root.

As further embodiment of the present invention, it is provided a therapeutic agent for treating ulcerative colitis having, as an active ingredient, an infused dry extract of peony root, an infused dry extract of a Chinese medicine formulation containing peony root, or especially, an infused dry extract of Jia-Wei-Xiao-Yao-San, Dang-Gui-Shao-Yao-San, Shao-Yao-Gan-Cao-Tang, or Gui-Zhi-Fu-Ling-Wan.

Hitherto, Chinese medicine formulations play an auxiliary role in treatment of administrating sulufasalazine, steroids, and the like, that is, used only for the purpose of the effect which brings mental rest, the effect of suppressing diarrhea, and the like. Among Chinese medicine formulations, a formulation of the present invention containing, as an active ingredient, dry powders of peony root, an infused dry extract of peony root, or an infused dry extract of a Chinese medicine formulation containing peony root is very effective in repairing damaged tissues in ulcerative colitis as apparent from the results of tests which will be described hereinlater and yet has no fear of exerting side effects as those of steroids. The invention therefore can provide an excellent agent for treating ulcerative colitis.

BEST MODE FOR CARRYING OUT THE INVENTION

Peony root (paeniae radix) as an active ingredient in the treatment agent provided by the present invention is obtained by drying the root of a perennial plant of the peony family (paeonia albiflora var. trichocarpa) grown in China, Korea, and Japan or a relative plant. Peony root is used as astringent, emollient, antispasmodic, analgesic, a drug for oversensitive to the cold, and a drug for dermatosis. Further, it is used for abdominal distension, abdominal pain, body pain, diarrhea, purulent tumor, and the like. Peony root is contained in Chinese medicine formulations such as Shao-Yao-Gan-Cao-Tang, Dang-Gui-Shao-Yao-San, Shi-Quan-Da-Bu-Tang (Juzen-taiho-to), Xiao-Qing-Long-Tang (Sho-seiryu-to), Da-Chai-Hu-Tang (Dai-saiko-to), Chai-Hu-Gui-Zhi-Tang (Saiko-keishi-to), Huang-Ling-Tang (Ogon-to), Si-Ni-San (Shigyaku-san), Dang-Gui-Jian-Zhong-Tang (Toki-kenvhu-to), Wen-Jing-Tang (Unkei-to), Zhen-Wu-Tang (Shimbu-to), Gui-Zhi-Shao-Yao-Zhi-Mu-Tang (Keishi-shakuyaku-chino-to), and the like.

The agent for treating ulcerative colitis provided by the present invention has, as an active ingredient, the dry powders of peony root or a Chinese medicine formulation containing peony root. Generally, a dose of 3 to 6 g of peony root is decocted and given per day. The infused dry extract of peony root can be prepared by, for example, a method of adding ten times (200 ml) of water to 20 g of finely chopped peony root, heating and refluxing the water and the chopped peony root for about three hours, filtering them, removing the residual material, and spray-drying the filtrate. It is preferable to administer the extract corresponding to 3 to 6 g per day as a dose of peony root.

As Chinese medicine formulations containing peony root, Jia-Wei-Xiao-Yao-San, Dang-Gui-Shao-Yao-San, Shao-Yao-Gan-Cao-Tang, Gui-Zhi-Fu-Ling-Wan, and the like can be mentioned.

Jia-Wei-Xiao-Yao-San is a formulation used for menopause symptom, menoxenia, autonomic imbalance, urethritis, chronic eczema, constipation, and the like and is prepared by, for example, 3.0 g each of Japanese angelica root, atractylodes rhizome, hoelen, and bupleurum root, 2.0 g each of glycyrrhiza, moutan bark, and gardenia fruit, and 1.0 g each of ginger and mentha herb. Generally, these crude drugs are administered in the form of either powders or decoction.

Dang-Gui-Shao-Yao-San is a formulation used for unidentified clinical syndrome, autonomic imbalance, menopause symptom, Meniere's disease, hypotension, hypertension, endocrinosis, rhinitis, eczema, dysmenorrhea, endometritis, suffer from piles, proctoptosis, and the like. For example, it is prepared by 3.0 g each of Japanese angelica root, and cnidium rhizome and 4.0 g each of peony root, atractylodes rhizome, hoelen, and alisma rhizome. These crude drugs are administered in the form of either powders or decoction. At present, extract granules of the formulation are also prepared and sold.

Shao-Yao-Gan-Cao-Tang is a formulation used for abnormal tension of rectus abdominis muscles, abnormal tension and pain of striated smooth muscles, and various algetic diseases with crick of limb or the like. 3.0 g each of peony root and glycyrrhiza are put into 600 ml of water. The water with the crude drugs is boiled down to 300 ml and filtered. The filtrate is administered in the form of a hot drink three times a day.

Gui-Zhi-Fu-Ling-Wan is a formulation used for various disorders caused by menoxenia, menopause symptom, neuronosis, neurosis, depression, eczema, urticaria, hemorrhoids, orchitis, and the like. Cinnamon fuigs, hoelen, moutan bark, peach kernel, and peony root are powdered, kneaded with honey, and pilled. Alternately, 4.0 g each of the above crude drugs are put into 600 ml of water. The water with the crude drugs is boiled down to 300 ml and filtered. The filtrate is administered in the form of a hot drink two or three times a day.

The agent for treating ulcerative colitis provided by the invention can take the forms of powders, granules, pills, tablets, capsules, and decoctions of trade drugs on the basis of any of the Chinese medicine formulations. When considering easiness of taking medicine, easiness of formulation, portability, and the like, a dry extract of a Chinese herbal medicine can be used as it is. Powders, granules, pills, fine granules, tablets, capsules, decoctions and the like obtained by processing the extract are preferably used.

A method of preparing an infused dry extract of any of the above-mentioned Chinese medicine formulations will be described with respect to the case of gui-zhi-fu-ling-wan as an example. The crude drugs according to the formulation and 600 ml of water are boiled down to 300 ml. The filtrate liquid is dried by a proper method such as spray dry or freezed dry. Powders of the extract of gui-zhi-fu-ling-wan are accordingly obtained, which may be used as they are as a Chinese extract.

Meanwhile, when the extract powders are processed into other forms, formulations in powders, granules, fine granules, pills, tablets, capsules, decoctions and the like can be prepared in accordance with a usual formulation preparing method by properly adding the following agents used for ordinary formulation: an excipient such as lactose, corn starch, or crystalline cellulose; a lubricant such as talc, magnesium stearate, or sucrose fatty acid ester; further, as necessary, a fluidity accelerator such as light anhydrous silicic acid or synthetic aluminum silicate; a disintegrator such as starch, hydroxypropyl starch, or carboxymethylcellulose calcium; a binder such as dextrin, acacua, methylcellulose, hydroxypropylcellulose, or polyvinyl pyrrolidone; a surfactant such as sodium lauryl sulfate, or polysorbate 80.

In case of compounding two or more kinds of Chinese herbal medicine extracts, the extracts may be prepared separately and compounded. Alternately, a formulation may be also prepared according to an usual method by compounding powders of respective extracts and adding excipient, lubricant, fluidity accelerator, disintegrator, binder, surfactant, and the like to the powders.

EXAMPLES

The present invention will now be specifically described by giving examples hereinbelow.

EXAMPLE 1

Water-infused Dry Extract of Peony Root

Purified water which is ten times as much as peony root is added to 10 g of peony root (Japanese Pharmacopoeia XIII). The peony root is infused at approximately 100° C. for three hours. The water and the peony root are filtered, the infusible material is removed, and the filtrate is spray-dried. The dried material is mixed and passed through a sieve, thereby obtaining 2.1 g of uniform powders of the water-infused dry extract of peony root.

EXAMPLE 2

Water-infused Dry Extract of Jia-Wei-Xiao-Yao-San 3.0 g each of Japanese angelica root, peony root, atractylodes rhizome, hoelen, and bupleurum root, 2.0 g each of glycyrrhiza, moutan bark, and gardenia fruit, and 1.0 g of ginger and mentha herb are finely chopped, mixed, and infused by adding purified water which is ten times as much as the crude drugs at approximately 100° C. for two hours. The mixture is filtered and the infusible material is removed. The filtrate is spray-dried. The dried materials are mixed and passed through a sieve, thereby obtaining 4.0 g of uniform powders of the water-infused dry extract of Jia-Wei-Xiao-Yao-San.

EXAMPLE 3

Water-infused Dry Extract of Dang-Gui-Shao-Yao-San 3.0 g each of Japanese angelica root and cnidium rhizome and 4.0 g each of peony root, atractylodes rhizome, hoelen, alisma rhizome are finely chopped, mixed and infused by adding purified water which is ten times as much as the crude drugs at approximately 100° C. for two hours. The mixture is filtered, the infusible material is removed, and the filtrate is spray-dried. The dried materials are mixed and passed through a sieve, thereby obtaining 2.9 g of uniform powders of the water-infused dry extract Dang-Gui-Yao-San.

EXAMPLE 4

Water-infused Dry Extract of Shao-Yao-Gan-Cao-Tang 3.0 g each of peony root and glycyrrhiza are finely chopped, mixed, and infused by adding purified water which is ten times as much as the crude drugs at approximately 100° C. for two hours. The mixture is filtered, the infusible material is removed, and the filtrate is spray-dried. The dried materials are mixed and passed through a sieve, thereby obtaining 0.9 g of uniform powders of the water-infused dry extract of Shao-Yao-Gan-Cao-Tang.

EXAMPLE 5

Water-infused Dry Extract of Gui-Zhi-Fu-Ling-Wan 4.0 g each of cinnamon fuigs, hoelen, moutan bark, peach kernel, and peony root are finely chopped, mixed, and infused by adding purified water which is ten times as much as the crude drugs at approximately 100° C. for two hours. The mixture is filtered, the infusible material is removed, and the filtrate is spray-dried. The dried materials are mixed and passed through a sieve, thereby obtaining 1.8 g of uniform powders of the water-infused dry extract of Gui-Zhi-Fu-Ling-Wan.

EXAMPLE 6

Peony Root Granules 10 g of peony root is finely chopped and milled, thereby obtaining powders. To 6 g of the powders, 6 g of lactose, 2.8 g of crystalline cellulose, and 0.2 g of magnesium stearate are added. The materials are mixed uniformly, shaped by using a compression shaping machine, milled by using a mill, and classified with a sifter, thereby obtaining granules.

EXAMPLE 7

Water-infused Dry Extract Tablet of Peony Root

To 25.6 g of the water-infused dry extract of peony root obtained in EXAMPLE 1, 5 g of lactose, 5 g of crystalline cellulose, 3 g of carboxymethylcellulose calcium, 1.2 g of light anhydrous silicic acid, and 0.2 g of magnesium stearate are added. The materials are mixed uniformly, and compressed and shaped by using a tablet making machine, thereby obtaining tablets each weighing 0.4 g.

EXAMPLE 8

Water-infused Dry Extract Capsule of Peony Root

To 25.6 g of the water-infused dry extract of peony root obtained in EXAMPLE 1, 2.4 g of corn starch and 2 g of light anhydrous silicic acid are added and granulated by mixing while adding ethanol. The obtained granules are dried under ventilation at 40° C. for one day and classified with a sifter. The water-infused dry extract granules of peony root are thus obtained. A No. 1 capsule is filled with 0.3 g of the granules. In the above manner, capsules are obtained.

EXAMPLE 9

Peony Root Powders 10 g of peony root is finely chopped, milled, and passed through a sieve, thereby obtaining powders. To 6 g of the powders, 4 g of lactose, 6 g of crystalline cellulose, and 2 g of corn starch are added. The materials are mixed uniformly and classified with a sifter, thereby obtaining powders.

EXAMPLE 10

Water-infused Dry Extract granules of Jia-Wei-Xiao-Yao-San

To 4.5 g of the water-infused dry extract of Jia-Wei-Xiao-Yao-San obtained in EXAMPLE 2, 2.5 g of lactose, 1 g of crystalline cellulose, 0.9 g of synthetic aluminum silicate, and 0.1 g of magnesium stearate are added. The materials are mixed uniformly, after that, shaped by using a compression shaping machine, milled by using a mill, and classified with a sifter, thereby obtaining granules.

EXAMPLE 11

Water-infused Dry Extract Granules of Dang-Gui-Shao-Yao-San

To 3.2 g of the water-infused dry extract of Dang-Gui-Shao-Yao-San obtained in EXAMPLE 3, 3.5 g of lactose, 1.2 g of crystalline cellulose, 1 g of light anhydrous silicic acid, 0.02 g of sucrose fatty acid ester, and 0.08 g of talc are added. The materials are mixed uniformly, after that, shaped by using a compression shaping machine, milled by using a mill, and classified with a sifter, thereby obtaining granules.

EXAMPLE 12

Water-infused Dry Extract Granules of Shao-Yao-Gan-Cao-Tang

To 1 g of the water-infused dry extract of Shao-Yao-Gan-Cao-Tang obtained in EXAMPLE 4, 3 g of lactose, 1.2 g of crystalline cellulose, 0.73 g of light anhydrous silicic acid, and 0.07 g of magnesium stearate are added. The materials are mixed uniformly, after that, shaped by using a compression shaping machine, milled using a mill, and classified with a sifter, thereby obtaining granules.

EXAMPLE 13

Water-infused Dry Extract Granules of Gui-Zhi-Fu-Ling-Wan

To 2 g of the water-infused dry extract of Gui-Zhi-Fu-Ling-Wan obtained in EXAMPLE 5, 4 g of lactose, 1.4 g of crystalline cellulose, and 0.1 g of magnesium stearate are added. The materials are mixed uniformly, after that, shaped by using a compression shaping machine, milled by using a mill, and classified with a sifter, thereby obtaining granules.

Effects of peony root and the Chinese medicine formulations containing peony root on treatment of ulcerative colitis will be described in detail hereinbelow on the basis of test examples.

Test Example 1

Groups each consisting of eight male Sprague-Dawley rats (7 weeks old) were used for the test. As drugs to be tested, the water-infused dry extract of peony root, the water-infused dry extract of Gui-Zhi-Fu-Ling-Wan, the water-infused dry extract of Dan-Gui-Shao-Yao-San, the water-infused dry extract of Jia-Wei-Xiao-Yao-San, and the water-infused dry extract of Shao-Yao-Gan-Cao-Tang were used.

Each of the dry extracts either dissolved or dispersed in water was orally administered to the rats once a day from four days before induction of colitis until the day before autopsy. The same amount of water was orally administered to a control group. Ulcerative colitis was induced by administering a solution in which 90 mg of trinitrobenzenesulfonic acid (TNB) was dissolved in 1.5 ml of 20% ethanol via anal pathway after four days since the start of administrating the drugs (Gastroenterology 96, pp 795 to 803 (1989)).

The rats were sacrificed on the seventh day after the induction of colitis and the following items were evaluated. The Dunnett test was used as a test of significance.

1) Wet Weight of Colon 8 cm of the colon from the anal was enucleated and its wet weight was measured.

2) Macroscopic Evaluation of Adhesion

Connective tissues in the tunica serosa and the like due to infiltration of inflammatory cells were macroscopically observed and scored in accordance with the following classifications.

0: no adhesion
1: slightly adhered easily abraded with fingers
2: strongly adhered
3: completely adhered 3) Macroscopic evaluation of severity The severity of colitis was evaluated according to the following classifications and scored.

0: no damage
1: slight hypertrophy of intestinal wall, no local congestion, no erosion of mucosa
2: congestion and hypertrophy of intestinal wall, or strong hypertrophy of intestinal wall with no congestion
3: one erosion accompanied by congestion and hypertrophy of intestinal wall
4: two or more erosions accompanied by congestion, or hypertrophy of intestinal wall
5: two or more damages or an damage of 2.5 cm or smaller in colon
6 to 9: when a damage is 2.5 cm or larger, score is increased by 1 each additional 0.5 cm of damage The results of the respective Chinese medicine formulations will be shown in the following tables 1 to 5.

TABLE 1

Treatment effects on ulcerative colitis by administrating dry extract of peony root

| Group | Wet weight of enteric canal ± S.E. (mg) | Adhesion ± S.E. | Severity ± S.E. |
|---|---|---|---|
| Control | 2136.0 ± 148.9 | 1.00 ± 0.26 | 7.76 ± 0.33 |
| 12.8 mg/kg per day | 1690.0 ± 82.3* | 0.71 ± 0.18 | 6.29 ± 0.29 |
| 25.6 mg/kg per day | 1777.7 ± 94.8 | 0.67 ± 0.21 | 5.83 ± 0.40 |
| 51.2 mg/kg per day | 1662.0 ± 105.8* | 0.57 ± 0.30 | 5.00 ± 0.52* |
| 102.4 mg/kg per day | 1498.0 ± 97.7** | 0.38 ± 0.26 | 4.50 ± 0.42** |
| 256 mg/kg per day | 2437.3 ± 231.2 | 2.57 ± 0.30 | 7.86 ± 0.34 |

*: $p < 0.05$
**: $p < 0.01$ compared with control group

As shown in Table 1, the values of all of the wet weight of enteric canal, adhesion, and severity in the oral administration of 12.8 mg to 102.4 mg/kg per day of the peony root dry extract are lower than these of the control group. Especially, the wet weight of enteric canal is significantly suppressed at the dose of administration of 12.8 mg/kg, 51.2 mg/kg and 102.4 mg/kg per day. The severity is significantly suppressed in the groups of administration of 51.2 mg/kg and 102.4 mg/kg per day. They are, however, not suppressed in the group of administration of 256 mg/kg per day as compared with the control group. It is consequently considered that the effective administration of the dry extract of peony root lies in a range from about 10 mg/kg to about 110 mg/kg per day.

TABLE 2

Treatment effects on ulcerative colitis by administrating dry extract of Jia-Wei-Xiao-Yao-San

| Group | Wet weight of enteric canal ± S.E. (mg) | Adhesion ± S.E. | Severity ± S.E. |
|---|---|---|---|
| Control | 2314.3 ± 133.3 | 1.63 ± 0.18 | 8.00 ± 0.27 |
| 235.0 mg/kg per day | 1686.4 ± 120.0** | 1.00 ± 0.31 | 4.86 ± 0.26** |

TABLE 2-continued

Treatment effects on ulcerative colitis by administrating dry extract of Jia-Wei-Xiao-Yao-San

| Group | Wet weight of enteric canal ± S.E. (mg) | Adhesion ± S.E. | Severity ± S.E. |
|---|---|---|---|
| 470.0 mg/kg per day | 1832.8 ± 44.0* | 1.40 ± 0.24 | 5.60 ± 0.24* |
| 940.0 mg/kg per day | 1884.0 ± 115.0* | 1.00 ± 0.31 | 6.30 ± 0.42* |

*: $p < 0.05$
**: $p < 0.01$ compared with control group

In the results of the Jia-Wei-Xiao-Yao-San dry extract as shown in Table 2, the wet weight of enteric canal and severity at the dose of 235 mg to 940 mg/kg per day are significantly suppressed. With respect to the adhesion as well, suppression tendency is recognized. The content of peony root in Jia-Wei-Xiao-Yao-San corresponds to 25.6 mg in 235 mg and 102.4 mg in 940 mg.

TABLE 3

Treatment effects on ulcerative colitis by administration of dry extract of Dang-Gui-Shao-Yao-San

| Group | Wet weight of enteric canal ± S.E. (mg) | Adhesion ± S.E. | Severity ± S.E. |
|---|---|---|---|
| Control | 2314.3 ± 133.3 | 1.63 ± 0.18 | 8.00 ± 0.27 |
| 128.0 mg/kg per day | 1791.7 ± 46.0** | 0.71 ± 0.29* | 5.86 ± 0.34** |
| 256.0 mg/kg per day | 1880.7 ± 76.0* | 0.86 ± 0.26 | 6.29 ± 0.47* |
| 512.0 mg/kg per day | 1853.0 ± 121.0* | 1.57 ± 0.20 | 6.29 ± 0.47* |

*: $p < 0.05$
**: $p < 0.01$ compared with control group

In the results of the Dang-Gui-Shao-Yao-San dry extract shown in Table 3, the wet weight of enteric canal and severity in the administration of 128 mg to 512 mg/kg per day are significantly suppressed. With respect to the adhesion, significant suppression is recognized in the administration of 128 mg/kg per day. In the other administrations as well, suppression tendency is recognized. The content of peony root in Dang-Gui-Shao-Yao-San corresponds to 25.6 mg in 128 mg and 102.4 mg in 512 mg.

TABLE 4

Treatment effects of ulcerative colitis by administration of dry extract of Shao-Yao-Gan-Cao-Tang

| Group | Wet weight of enteric canal ± S.E. (mg) | Adhesion ± S.E. | Severity ± S.E. |
|---|---|---|---|
| Control | 2136.0 ± 148.9 | 1.00 ± 0.26 | 7.76 ± 0.33 |
| 71.0 mg/kg per day | 1621.0 ± 122.6* | 0.83 ± 0.40 | 6.33 ± 0.42 |
| 142.0 mg/kg per day | 1606.5 ± 118.7* | 0.67 ± 0.33 | 5.33 ± 0.49* |

*: $p < 0.05$ compared with control group

In the results of the Shao-Yao-Gan-Cao-Tang dry extract as shown in Table 4, the wet weight of enteric canal at the dose of 71 to 142 mg/kg per day is significantly suppressed. It is recognized that the severity is significantly suppressed at the dose of 142 mg/kg per day and tends to be suppressed at the dose of 71 mg/kg per day. It is recognized that the adhesion tends to be suppressed at both of the administered doses. The content of peony root in Shao-Yao-Gan-Cao-Tang corresponds to 25.6 mg in 71 mg and 51.2 mg in 142 mg.

TABLE 5

Treatments effects on ulcerative colitis by the administration of dry extract of Gui-Zhi-Fu-Ling-Wan

| Group | Wet weight of ± S.E. enteric canal (mg) | Adhesion ± S.E. | Severity ± S.E. |
|---|---|---|---|
| Control | 2478.3 ± 185.0 | 3.00 ± 0.40 | 6.57 ± 0.53 |
| 40.6 mg/kg per day | 2007.7 ± 105.7* | 2.00 ± 0.63 | 5.00 ± 0.52 |
| 203.0 mg/kg per day | 1915.4 ± 115.5* | 1.14 ± 0.51 | 5.00 ± 0.44 |
| 406.0 mg/kg per day | 1804.0 ± 94.9* | 1.43 ± 0.69 | 4.00 ± 0.22** |

*: $p < 0.05$
**: $p < 0.01$ compared with control group

In the results of the Gui-Zhi-Fu-Ling-Wan dry extract shown in Table 5, the wet weight of enteric canal was significantly suppressed at the dose of 40.6 mg to 406 mg/kg per day. It was recognized that the severity is significantly suppressed at the dose of 406 mg/kg per day and tends to be suppressed at the other administered doses. With respect to the adhesion, suppression tendency is recognized at any of the administered doses. The content of peony root in Gui-Zhi-Fu-Ling-Wan corresponds to 12.8 mg in 40.6 mg and 128 mg in 406 mg.

As will be understood from the above-mentioned results, by oral administrating peony root and the Chinese medicine formulations containing peony root, ulcerative colitis can be suppressed. When the administered dose of the peony dry extract exceeds 128 mg/kg per day, however, the suppression effect is lost. It is therefore preferable that the ulcerative colitis treating agent of the present invention is prescribed so that the peony root dry extract of about 10 mg/kg to 110 mg/kg per day is administered.

Industrial Applicability

As described above, the ulcerative colitis treating agent containing peony root provided by the present invention has the excellent effects on treating ulcerative colitis.

The ulcerative colitis treating agent of the present invention is therefore very effective in repairing damaged tissues of ulcerative colitis and yet has no need of fear of exerting the side effects as those of steroids. Thus, it is useful for treating ulcerative colitis.

What is claimed is:

1. A method for treating ulcerative colitis comprising administering an infused dry extract of a member of the group consisting of Jia-Wei-Xioa-Yao-San, Dang-Gui-Shao-Yao-San, Gui-Zhi-Fu-Ling-Wan, and mixtures thereof in a daily effective dose, wherein the infused dry extract contains peony root as an active ingredient.

2. The method of treating ulcerative colitis according to claim 1, wherein the infused dry extract is administered in the form of powders, granules, pills, tablets, capsules, or decoctions in combination with a pharmaceutically acceptable excipient or diluent.

3. The method of treating ulcerative colitis according to claim 1, wherein the infused dry extract is in combination with an infused dry extract of Sha-Yao-Gan-Cao-Tang.

4. The method of treating ulcerative colitis according to claim 1, wherein said infused dry extract is in combination with a pharmaceutically acceptable excipient or diluent.

5. The method of treating ulcerative colitis according to claim 1, wherein the infused dry extract combination is in combination with a pharmaceutically acceptable excipient or diluent.

6. The method of treating ulcerative colitis according to claim 1, wherein said daily effective dose is 3 to 6 grams/day of said active ingredient.

7. The method of treating ulcerative colitis according to claim 3, wherein said daily effective dose is 3 to 6 grams/day of said active ingredient.

8. The method of treating ulcerative colitis according to claim 4, wherein said daily effective dose is 3 to 6 grams/day of said active ingredient.

9. The method of treating ulcerative colitis according to claim 5, wherein said daily effective dose is 3 to 6 grams/day of said active ingredient.

10. The method of treating ulcerative colitis according to claim 2, wherein said daily effective dose is 3 to 6 grams/day of said active ingredient.

* * * * *